United States Patent [19]

Dürr et al.

[11] 4,032,803

[45] June 28, 1977

[54] HAND TOOL FOR CREATING AND APPLYING ULTRASONIC VIBRATION

[75] Inventors: Walter Dürr, Bissingen; Mathias Müller, Oberstenfeld, both of Germany

[73] Assignee: Dürr-Dental KG., Germany

[22] Filed: Apr. 12, 1976

[21] Appl. No.: 676,009

Related U.S. Application Data

[63] Continuation-in-part of Ser. No. 459,164, April 8, 1974, abandoned, which is a continuation of Ser. No. 288,880, Sept. 13, 1972, abandoned.

[30] Foreign Application Priority Data

Aug. 28, 1972 Switzerland .................. 012680/72

[52] U.S. Cl. .................. 310/8.1; 310/8.3
[51] Int. Cl.² .................. H01L 41/04
[58] Field of Search .............. 310/8.1, 8.2, 8.3, 9.1, 310/9.4, 26; 128/24 A, 62 A; 32/50, 58, 46, DIG. 4; 318/116, 118

[56] References Cited

UNITED STATES PATENTS

| | | | |
|---|---|---|---|
| 3,375,820 | 4/1968 | Kuris et al. | 310/8.1 UX |
| 3,518,766 | 7/1970 | Burt | 310/8.1 X |
| 3,657,874 | 4/1972 | Imahashi | 310/8.1 X |
| 3,679,918 | 7/1972 | Keizi | 310/8.1 |
| 3,828,770 | 8/1974 | Kuris et al. | 310/8.1 X |
| 3,843,897 | 10/1974 | Mishiro | 310/8.7 X |

Primary Examiner—Mark O. Budd
Attorney, Agent, or Firm—Robert E. Burns; Emmanuel J. Lobato; Bruce L. Adams

[57] ABSTRACT

A hand held device for generating ultrasonic vibrations comprises an elongate tubular casing having therein a piezoelectric vibratory element comprising an elongate bar of piezoelectric material and a generator that develops an electrical signal having a predetermined ultrasonic frequency that excites the piezoelectric vibratory element into ultrasonic vibration. The piezoelectric vibratory element also functions as the dielectric of a capacitor which constitutes part of the generator and which determines the ultrasonic frequency of the electrical signal output of the generator. A work tool protrudes from the casing and is vibrationally coupled to the piezoelectric vibrator element by a vibratory rod which transmits the vibrations from the piezoelectric vibratory element to the work tool. A cooling system is disposed within the casing and flows a cooling agent through the device to cool both the piezoelectric vibratory element and the generator and the cooling agent is discharged from the device in atomized form through an opening in the work tool. Manually operable control means on the casing controls the generator and the cooling agent.

22 Claims, 6 Drawing Figures

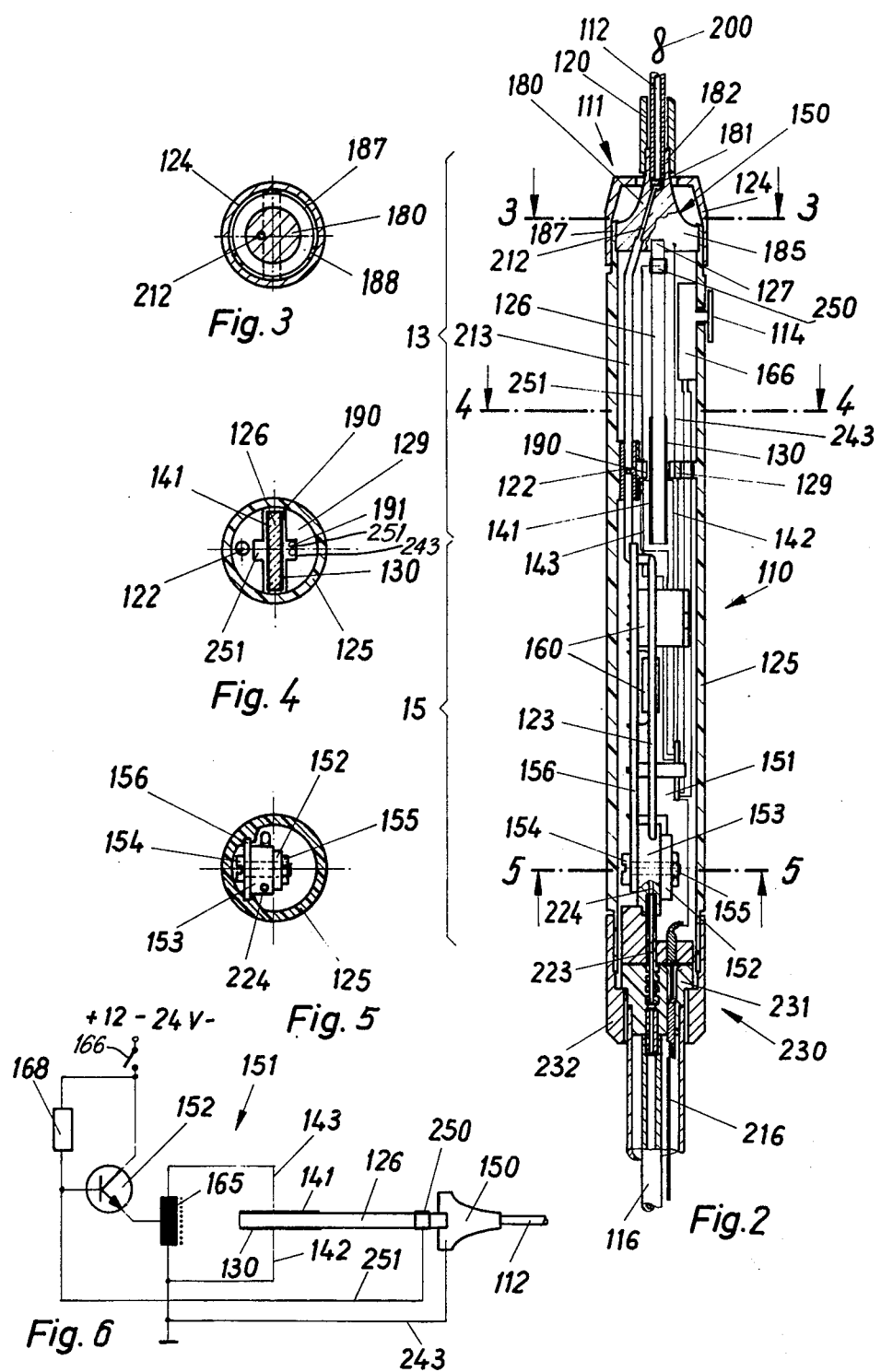

HAND TOOL FOR CREATING AND APPLYING ULTRASONIC VIBRATION

REFERENCE TO PRIOR APPLICATIONS

This application is a continuation-in-part of application Ser. No. 459,164 filed Apr. 8, 1974 now abandoned which in turn was a continuation of application Ser. No. 288,880 filed Sept. 13, 1972, now abandoned.

FIELD OF INVENTION

The invention relates to a device for generating and applying ultrasonic vibration especially for dental, medical or cosmetic use comprising a piezoelectric vibrator element which is contained in an elongate hand tool and is vibrationally connected to a rod which propagates the ultrasonic vibration and extends out of the end of the hand tool and a generator which creates electrical oscillations for exciting the piezoelectric vibrator element.

BACKGROUND OF INVENTION

Devices operating on the ultrasonic principle have been used for quite some time especially in dentistry where they are useful for removal of tartar from the teeth. In such devices, nickel rods or ferrites are used to generate vibrations of ultrasonic frequency usually in the range of 20–30 kHz. These vibrations are used to drive the work tool that loosens the tartar from the teeth.

A known type of piezoelectric dental cleaning device has a piezoelectric vibrator element in the shape of a cylindrical tube which occupies almost the entire casing of the hand tool. The oscillator for exciting the piezoelectric vibrator element is a separate external unit which is connected with the vibrator element by a shielded cable capable of transmitting high frequencies.

The known devices are relatively large and heavy and what is most important take up considerable room which is particularly inconvenient in view of the notorious shortage of space around a dentist's chair. The generator or oscillator together with its power supply and controls especially those for tuning and volume control were housed in a relatively bulky case or container which due to a lack of space could not be accommodated at the usual dentist's chair. One solution was to install the oscillator with its power supply and controls in a separate cabinet at one side of the room with a relatively long shielded cable extending from the oscillator to the hand held tool containing the piezoelectric vibrator element. Another solution was to install the tartar remover at a separate chair so that the dentist could have the switch and manual controls of the oscillator more conveniently located. However, this entailed the expense of an additional chair and room to accommodate it and was also inconvenient for a patient requiring regular dental work and tartar removal since it meant that he would have to change chairs.

SUMMARY OF INVENTION

It is an object of the invention to do away with the drawbacks of the known devices and to create a compact self contained efficiently operating ultrasonic device that can be installed and used in any location. In accordance with the invention the vibrator element and a miniaturized oscillator for energizing it are united into a single structural unit, both components being contained in a slender tubular casing of a size and shape conveniently to be held in the hand. The oscillator or generator is spacially separated from the vibrator element in the casing and is vibrationally insulated from it as well so that it is not deleteriously affected by the mechanical vibration produced by the vibrator element. A unit of this type which makes use of modern components of industrial electronics may be made very small and makes possible a considerable saving of space as compared with the known type of equipment. What is most significant is that by eliminating a separate external generator and a shielded line from the generator to the hand tool the invention makes it possible for the ultrasonic hand tool to share the dental chair area with all of the other instruments without creating any problems in the use of space. As a rule, the low voltage direct current required for the generator is already present at the dental chair or can be generated by equipment which may be located in any convenient place. Inconveniences resulting from the use of a high frequency line between an external generator and the hand tool are thus avoided. The control for turning the device on and off is located in the hand tool itself. Since the piezoelectric vibrator element, the generator and connecting and control circuitry are all contained in the casing which can be formed of metal or metal coated plastic, proper shielding of oscillations is achieved.

The piezoelectric vibrator element can be the frequency determining element of the generator which provides excitation for the vibrator element whereby the total layout is further simplified and problems of tuning, temperature and frequency are eliminated. As the vibrator element and the generator lie close together although spacially separated and vibrationally insulated, the connecting leads between them can be very short and are fully protected by the casing in which the vibrator element and generator are both contained. By making the leads flexible, the transmission of mechanical vibration from the vibrator element to the generator through the leads is avoided.

A fluid medium especially water which is customarily available at the dental chair is supplied to the hand tool through flexible tubing and serves the multiple purpose of cooling the generator and vibrator element and washing away tartar or other particles dislodged by the tool. A fluid line extending longitudinally through the casing and comprising a rearward portion adjacent the generator and a forward portion adjacent the vibrator element is designed so as to be vibrationally insulated to avoid transmitting mechanical vibration from the vibrator element to the generator.

Particularly suitable for piezoelectric vibrator elements are piezoelectric ceramics which propagate mechanical vibrations under the influence of an alternating current applied to their electrodes, such vibrations being transmitted to a work tool at the forward end of the casing. Optimum conditions of frequency, power input, power output and amplitude of vibration can be achieved by the use of ceramic materials such as lead zirconate-titanate or barium-titanate.

BRIEF DESCRIPTION OF DRAWINGS

Further details of the invention will appear from the following description of a preferred embodiment shown by way of example in the accompanying drawings in which:

FIG. 2 is a longitudinal section through a preferred embodiment of a hand tool for tartar removal comprising a piezoelectric vibrator element and an internal generator both housed in a tubular casing;

FIG. 3 is a cross section taken along line 3—3 in FIG. 2;

FIG. 4 is a cross section taken along the line 4—4 in FIG. 2;

FIG. 5 is a cross section taken along the line 5—5 in FIG. 2;

FIG. 6 is a circuit diagram of an electrical circuit for the generator, piezoelectric element and connecting circuitry of the device of FIGS. 2 to 5.

DESCRIPTION OF PREFERRED EMBODIMENT

Figure 1:
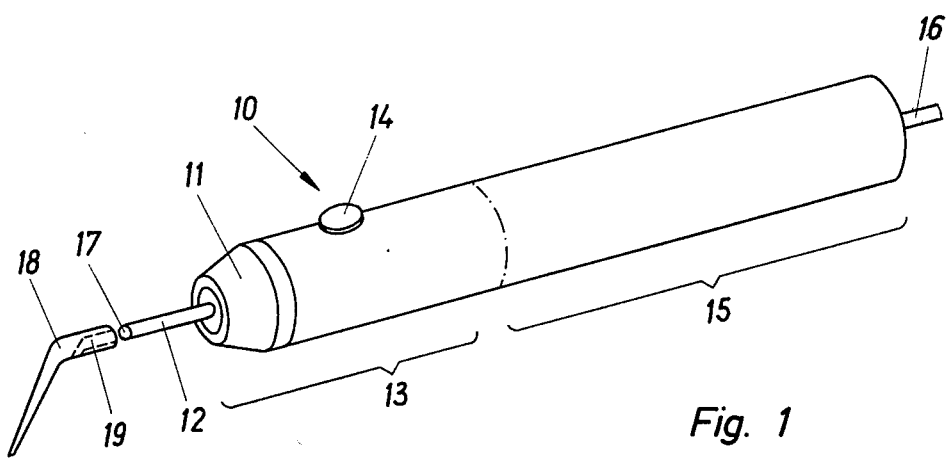
FIG. 1 is a perspective view of a hand tool in accordance with the invention designed particularly for the removal of tartar from teeth.

FIG. 1 is a slightly enlarged perspective view of a hand tool 10 in accordance with the invention which is preferably designed for the removal of tartar from the teeth by ultrasonic vibration but which may also be used for other operations such as manicuring, the removal of defective parts from pressure plates, the atomization of liquids, etc. The hand tool comprises a slender elongate tubular casing of a size and shape conveniently to be held in the hand of a user. Extending outwardly from the forward end 11 of the hand tool is a hollow rod 12 to which a work-tip 18 is attached. A forward compartment 13 of the casing contains the piezoelectric element which generates ultrasonic vibrations which are transmitted through the rod 12 to the work-tip 18. A rearward compartment 15 of the casing contains an electrical generator for producing an alternating ultrasonic signal to excite the piezoelectric vibrator element. The generator is controlled by a manually operable knob 14 which is provided on the casing in a location convenient for operation by a user. A flexible hose 16 brings in cold water which flows through a passageway extending longitudinally through the casing and through the hollow rod 12 to a hole 19 drilled in the work-tip 18. On leaving the hole 19, the water is atomized by the vibration of the work-tip and is used to wash away the loosened particles of tartar from the teeth. In flowing through the casing, the water cools the generator in the rearward compartment 15 and also the piezoelectric element in the forward compartment 13. Connected in parallel with the hose 16 is an electrical cable for supplying to the generator a low voltage electrical current which for example may be 6, 12 or 24 volts. Such current is customarily available at a dental chair. For special uses the device may also be battery operated in which case the outside source of electrical power is not needed.

The embodiment of the invention shown in FIGS. 2 to 6 is an elongated hand tool 110, the outward form of which corresponds in essence to the device of FIG. 1. The hand tool comprises a slender elongate tubular casing 125 which is made of plastic but is internally coated by a suitable process with metal which acts as a shield for the piezoelectric element, the electrical generator and connecting circuitry housed in the casing. Alternatively, the casing may be made of aluminum or other suitable metal. A forward compartment 13 of the casing contains the piezoelectric vibrator element 126 while the generator 151 is in a rearward compartment 15.

In the illustrated embodiment, the piezoelectric vibrator element 126 comprises an elongate bar of piezoelectric material and especially a piezoelectric ceramic for example a titanate and in particular a lead zirconate-titanate (PZT) or a barium-titanate. The material may also contain selected additives to secure the desired properties at the discretion of the manufacturer. It is important in choosing the material that it possesses piezoelectric properties and that it propagates mechanical vibrations of a desired form and amplitude when acted upon by a high frequency voltage. Especially suitable for dental use are vibrations of the order of 40 to 80 kHz. As may be seen from FIGS. 2 and 4 the vibrator element 126 is designed in the form of an elongate bar having a uniform rectangular cross section of which the width is substantially greater than the thickness. As shown in FIG. 4 the width of the bar is approximately five times its thickness. The proportions are selected to give maximum amplitude at the desired frequency.

At its forward end the vibrator element 126 is secured to a connector 150 in the head 111 of the device. The connector 150 serves the multiple purpose of positioning the forward end of the vibrator element, providing for an electrical connection and coupling the vibrator element to a tube 112 on which a work-tip 18 (FIG. 1) is mounted. As illustrated in FIG. 2, the forward end of the vibrator element 126 is received in an appropriate slot in the base of the connector 150 and is cemented in place. The connector 150 may for example be made of aluminum and comprises a cylindrical base portion 185 and a tapered nose portion 180. The front end of the nose portion has a drilled hole 181 having slotted side walls 182 and into which the vibrating rod here shown as a tube 112 is inserted. A sleeve nut 120 screwed onto a threaded portion of the nose holds the tube 112 in place. The exchangeable tube 112 is designed to hold a work-tip 18 or may itself form a work tool or tip for whatever use is to be made of the device. The nose portion of the connector 150 is in the shape of a funnel or concave cone as seen in FIG. 2 so as to concentrate and amplify the vibrations transmitted from the piezoelectric vibrator element 126. The nose portion 180 and base portion 185 of the connector 150 are integral with one another.

The cylindrical base portion 185 of the connector 150 is inserted in the front end of the tubular casing 125. A forward end portion 187 of the tubular casing is longitudinally slotted as indicated at 188 and is externally threaded to receive a nut 124 which screws onto the threaded end portion of the casing and contracts it to hold the base portion 185 of the connector in the forward portion of the housing 125. The vibrator assembly consisting of the piezoelectric vibrator element 126, the connector 150, tube 112 and nut 120 is tuned in such a way that the base portion 185 of the connector lies within a node of vibration so that the wave form and intensity are not transmitted by the fastenings and no appreciable vibrations are transferred to the housing 125.

From the connector 150 the piezoelectric vibrator element 126 extends rearwardly longitudinally in the housing 125 and passes through an aperture 190 of matching cross section but slightly larger than the vibrator element. As seen in FIGS. 2 and 4 the aperture 190 is located in a housing support 129 which may for instance be designed as a partition. The support 129 positions the vibrator element 126 and protects it from breakage, for example in the event the hand tool is dropped. The support is likewise located in the area of a vibration node so that there is no appreciable transfer of vibration from the vibratory element to the housing. The aperture 190 has lateral recesses 191 through which electric leads 243 and 251 (described below) can pass. Moreover, the housing support 129 is provided with a hole extending longitudinally of the casing to receive a flexible hose 122 for supplying water to the work-tip of the tool as described below.

The generator or oscillator 151 for supplying an alternating signal of supersonic frequency to energize the vibrator is mounted on a supporting plate 156 in the rearward compartment 15 of the casing. A printed circuit is provide in known manner on the underside of the supporting plate 156 and schematically represented electrical circuit elements 160 are secured to the plate 156 in customary manner. As shown schematically in FIG. 6 the generator comprises a vibration resistant npn power transistor 152, the collector of which is connected to the positive pole of a low voltage power source for example 12 to 24 volts. A switch 166 in the power supply circuit is operable by a manually operable external knob 141 provided on a forward portion of the casing 125 in convenient position for actuation by a user of the hand tool to turn the generator 151 on and off. The base of the transistor 152 is likewise connected to the positive pole of the power source through a working resistor 168. The emitter of the transistor 152 is connected to an intermediate tap of an inductor 165, the lower terminal of which is connected to ground which is also connected to the negative pole of the power source. The lower terminal of the inductor 165 is also connected by a lead 142 to an electrode 130 of the piezoelectric element 126 while the upper terminal of the inductor 165 is connected by a lead 143 to the opposite electrode 141 of the piezoelectric element 126. As illustrated in FIGS. 2 and 4 the electrodes 130 and 141 are on opposite sides of the flat rectangular bar of piezoelectric material. The electrodes 130 and 141 with the dielectric piezoelectric material between them thus comprise a capacitor which together with the inductor 165 form the LC component of the circuit.

The vapor coated electrodes 130 and 141 are located in the area of the support 129 within a vibration node of the piezoelectric element. The leads 142 and 143 which are connected with the electrodes 130 and 141, for example by soldering, are flexible and thus insensitive to vibration. The leads 142 and 143 thus electrically connect the generator with the piezoelectric vibratory element while insulating the generator from the vibrations. Moreover, location of the electrodes 130 and 141 at a node of vibration of the piezoelectric element further inhibits the transmission of vibrations from the vibrating element to the generator.

A further vapor coated silver electrode 250 is placed around the front end of the piezoelectric element 126 and is connected by a feedback line 251 to the base of the transistor 152. The metallic connector 150 which is secured to the front end of the piezoelectric element as described above and is spaced a small distance from the electrode 250 is connected to ground and hence to the lower terminal of the inductor 165 by a lead 243. The leads 243 and 251 pass through the lateral recesses of the aperture 190 in the support 129. The leads 243 and 251 are connected to the piezoelectric element 126 at a node of vibration and are moreover flexible so as to inhibit the transmission of mechanical vibration thereby further insulating the generator vibrationally from the piezoelectric element. Through the connector 150 and lead 243 the casing 125 (if metallic) or the metallic coating of the casing (if plastic) is grounded so that the piezoelectric element, the generator and the connecting circuitry between them are fully shielded.

A cooling fluid line extends longitudinally through the casing to provide cooling fluid for the generator and for the piezoelectric element and to deliver fluid — usually water — to the work-tip at the forward end of the casing. Fluid is supplied through a flexible hose or tube 116 connected to the rearward end of the casing. A cooling fluid line 223 extends from the supply tube 116 to a heat trap 153 to which the power transistor 152 is thermoconductively connected by means of a screw 154. The cooling fluid passes through a passage 224 of the heat trap to the forward side of which a cooling fluid tube 123 is connected. The cooling fluid tube 123 has an offset bend passing through the support plate 156 and is connected at its forward end with a flexible tube 122 formed for example of elastic material. The flexible tube 122 passes through a hole in the support 129 which has described above is located at a node of vibration of the piezoelectric element. At its forward end the tube 122 is connected with a tube 213 which connects with a passage 212 running obliquely through the connector member 150. The passage 212 opens into the drilled hole 181 in which the tube 112 is received and is thereby connected with the tube 112. Thus, water or other fluid supplied through the hose 116 passes through the passageway 223, the hole 224 of the heat sink 153, the longitudinally extending tubing 123, flexible hose 122, tubing 213 and passageway 212 to the tube 112 which as described above may comprise the work-tip of the tool or to which a work-tip 18 is affixed as illustrated in FIG. 1. The fluid thus delivered to the work-tip serves to cool both the generator 151 and the piezoelectric element 126. The flexible hose 122 connecting the forward portion 213 of the tubing with the rearward portion 123 provides insulation to inhibit the transmission of mechanical vibration from the piezoelectric vibratory element in the forward compartment 13 of the casing to the generator or oscillator in the rearward compartment 15.

Preferably, the switch 166 operated by the control knob 114 on a forward portion of the casing as described above controls not only the operation of the generator 151 but also the supply of cooling fluid by means of a solenoid valve which is located either in the casing 125 or externally of the casing, suitable electrical connections being provided between the switch 166 and the valve.

Low voltage current is supplied to the generator through a line 216 extending from the rear end of the casing 125. The line 216 comprises a flexible low voltage electric cord which parallels or is incorporated with the flexible tube 116 which supplies cooling fluid to the hand tool. The line 216 is connected with a suitable source of low voltage current for example 12 to 24 volts which is ordinarily available at a dental chair.

Connection of the cooling fluid line 116 and the power supply line 216 to the hand tool is effected by a plug connection 230 comprising a plug 231 which permits easy connecting and disconnecting of both the cooling fluid line 116 and the electric power and control lines 216. The plug 231 is held in place by a sleeve nut 232 screwed onto a reduced threaded rear end of the casing 125. In the event the solenoid valve for controlling the cooling fluid is located externally of the casing, for example at the supply to which the cooling fluid line 116 is connected, the electric line 216 includes a control line for the valve. In any event the electrical line 216 is a low voltage, direct current or low frequency line which does not require special insulation or shielding.

In the construction illustrated in FIG. 2 with sleeve nuts at both ends of the casing 125 the piezoelectric vibratory element comprising the bar 126 of ceramic material and the connector 150 can be inserted into the forward compartment 13 through the forward end of the casing while the generator 151 can be inserted in the rearward compartment 15 from the rear end of the casing. This facilitates assembly of the hand tool.

The hand tool in accordance with the invention operates as follows. When the device is turned on by means of the knob 114, the generator 151 is connected with the electrical source by the switch 166 so that the generator produces an ultrasonic electric signal to energize the piezoelectric element 126 causing it to vibrate at a frequency determined by the dimensions of the piezoelectric element and the frequency of the LC circuit comprising the inductor 156 and the capacitor formed by the electrodes 130 and 141 on opposite sides of the piezoelectric element. The frequency is preferably between 40 and 80 kHz. The resonant frequency of the piezoelectric element is propagated over the feedback electrode 250 to the base of the transistor 152. The piezoelectric element is thus the frequency determining element of the generator 151 by which the piezoelectric element is excited. The device is thus self-tuning so that no special tuning circuits or controls are required.

Under the influence of the electrical oscillations produced by the generator 151 the piezoelectric vibrator element 126 is caused to vibrate mechanically by virtue of a reciprocal piezoelectric effect. These mechanical vibrations are transmitted through the connector 150 and especially through the concentrating and amplifying funnel part 180 to the tube 112 and consequently to the work-tip. The tube 112 propagates a combined longitudinal-transverse vibration, the longitudinal vibration having a greater amplitude so that the vibration has a shape similar to a figure 8 represented symbolically as indicated by the reference numeral 200 in FIG. 2. By means of the corresponding vibrations of the work tool, tartar may be removed from the teeth or cleaning and polishing operations may be performed. The cooling fluid, especially water, which flows through the line 116 also flows through the heat trap 153 of the generator 151, the line 123, flexible tubing 122, line 213 and duct 212 to the tube 112 and thus to the work site where it is atomized and serves to cool and wash away the particles that have been removed from the tooth. At the same time it conducts away the heat generated in the device so that it is possible to achieve the desired output from the generator for this small piece of equipment using about 8 to 10 watts without any detrimental effects on the operation of the equipment.

The circuits may also be provided with further elements at the discretion of one skilled in the art or other types of oscillator circuits may be used. It would also be suitable to use other piezoelectric vibrator elements which would in the main be differentiated from magnetostrictive vibrators by the fact that they provide effective cutting power with a relatively low input of electrical power.

The device in accordance with the invention is suitable not only for the removal of tartar from teeth but also for other applications such as for cosmetic treatment or for surgical uses. It has also been found that liquids can be effectively atomized by the use of vibrators of this type especially aerosols for inhalation purposes. However, it is also possible to atomize fuels in carburetors and in smaller combustion engines it has been found possible to achieve considerably higher performance in this manner. It is possible to design the rod extending out the end of the device in a manner suitable for any of these purposes or a suitable work tool may be attached to the rod. The work tool may accordingly be a tartar removing tool, an atomizing nozzle, a manicuring tool, a surgical tool, an engraving needle, a pressure plate scrapper or the like.

What we claim and desire to secure by Letters Patent is:

1. A hand tool for creating and applying ultrasonic vibration, especially for dental, medical and cosmetic use, comprising:
  a. handle means comprising a tubular casing of slender elongate form to facilitate holding and manipulation of the hand tool by a user, said casing having a forward end and a rearward end,
  b. a piezoelectric vibratory element mounted in said casing for vibrational movement therein, said element comprising an elongate bar of piezoelectric material extending longitudinally in a forward portion of said casing,
  c. a vibratable work-tip disposed forwardly of the forward end of said casing and means coupling said work-tip with said piezoelectric vibratory element to transmit vibration from said element to said work-tip,
  d. signal generating means disposed in a rearward portion of said casing, said signal generating means comprising an oscillator for generating an alternating electrical signal of ultrasonic frequency, said generating means being spaced from and mechanically vibrationally insulated from said piezoelectric vibratory element in said forward portion of said casing,
  e. circuit means wholly within said casing for electrically connecting said signal generating means with said piezoelectric vibratory element to apply said ultrasonic alternating electric signal to said piezoelectric vibratory element and thereby excite said element into ultrasonic vibration and by such vibration to produce ultrasonic vibration of said work-tip, said circuit means comprising flexible leads from said signal generating means to said piezoelectric vibratory element to provide electrical connection but mechanical vibrational insulation between said generating means and said vibratory element,
  f. electrical conductor means electrically connected with said signal generating means and extending from the rearward end of said casing for supplying low voltage direct current to said signal generating means in said casing, and
  g. fluid supply means comprising flexible fluid conduit means extending from the rearward end of said casing to a fluid supply, and fluid passage means extending longitudinally through said casing from said fluid conduit means at the rearward end of the casing to the forward end of the casing to deliver fluid to said work-tip, said fluid passage means comprising a rearward portion to heat receiving relation to said signal generating means to cool the same, a forward portion in heat receiving relation to said vibratory element to cool the same, and a flexible intermediate portion between said rearward portion and said forward portion to provide continuity of said fluid passage means while providing mechanical vibrational insulation between said vibratory element and said signal generating means.

2. A hand tool according to claim 1, comprising manually operable means on said casing for controlling the supply of current to said signal generating means and for controlling the supply of fluid to said fluid passage means.

3. A hand tool according to claim 1, in which said circuit means comprise electrodes on opposite sides of said bar of piezoelectric material and electrical connections for supplying a signal from said signal generating means to excite said vibratory element and a further electrode on said bar of piezoelectric material with electrical connection from said further electrode back to said signal generating means to control the frequency of said signal.

4. A hand tool according to claim 1, in which said casing comprises a metallic sheath enclosing and electrically shielding said signal generating means, said piezoelectric vibratory element and said circuit means.

5. A hand tool for creating and applying ultrasonic vibration especially for dental, medical and cosmetic use, comprising:
  a. handle means comprising a tubular casing of slender elongate form to facilitate holding and manipulation of the hand tool by a user, said casing having a forward end and a rearward end,
  b. a piezoelectric vibratory element comprising an elongate bar of piezoelectric material and means mounting said bar in a forward portion of said tubular casing with the bar extending longitudinally of the casing, said mounting means comprising support means in said casing supporting said bar at a node of vibration so as to inhibit transmission of vibration to said casing,
  c. a vibratable work-tip disposed forwardly of the forward end of said casing and means coupling said work-tip with said vibratory element to transmit vibration from said element to said work-tip,
  d. signal generating means housed in a rearward portion of said casing, said signal generating means comprising an oscillator for generating an alternating electrical signal of ultrasonic frequency, said generating means being spaced from and mechanical vibrationally insulated from said piezoelectric vibratory element in said forward portion of said casing,
  e. circuit means wholly within said casing for electrically connecting said signal generating means with said piezoelectric vibratory element to apply said ultrasonic alternating electric signal to said piezoelectric vibratory element and thereby excite said element into ultrasonic vibration and to feed back a control signal from said piezoelectric element to said generating means to control the frequency of said oscillator, said circuit means including flexible leads providing electrical connections between said generating means and said piezoelectric vibratory element while inhibiting transmission of mechanical vibration from said vibratory element to said signal generating means,
  f. said casing comprising a metallic sheath enclosing and electrically shielding said signal generating means, said piezoelectric vibratory element and said circuit means, and
  g. means for supplying a fluid cooling medium to said signal generating means.

6. A hand tool according to claim 5, in which said coupling means comprises a rearward portion fixed to the forward end of said bar of piezoelectric material, a tapered forward portion for amplifying the amplitude of vibration in transmitting vibration from said bar to said work-tip and means for securing said work-tip to said forward portion.

7. A hand tool according to claim 6, in which said securing means comprises means for removably securing said work-tip to said coupling means, whereby said work-tip is removable and replaceable.

8. A hand tool according to claim 5, comprising means for supplying low voltage power to said signal generating means and manually operable means on said casing for controlling the supply of power to said signal generating means and thereby controlling operation of said signal generating means.

9. A hand tool according to claim 5, in which said bar of piezoelectric material is of uniform rectangular cross section with greater width than thickness.

10. A hand tool according to claim 9, in which said signal generating means comprises an inductor, and said circuit means comprises control electrodes affixed to opposite sides of said bar of piezoelectric material at a node of vibration of said bar, whereby said electrodes with said piezoelectric material of said bar between them forms a capacitor, and means connecting said inductor with said control electrodes, whereby said inductor and said capacitor form an LC circuit of said oscillator.

11. A hand tool according to claim 10, in which said inductor has end terminals connected respectively with said electrodes and an intermediate tap, and in which said signal generating means comprises an npn power transistor, means connecting the emitter of said transistor with said tap and the collector of said transistor with the positive terminals of a voltage supply and means connecting one of said end terminals of said inductor with the negative terminal of said voltage supply.

12. A hand tool according to claim 11, in which said circuit means further comprises a feedback electrode affixed on said bar of piezoelectric material near its forward end and means connecting said feedback electrode with the base of said transistor to regulate the frequency of said alternating electric signal.

13. A hand tool for creating and applying ultrasonic vibration especially for dental, medical and cosmetic use, comprising:
  a. handle means comprising a tubular casing of slender elongate form to facilitate holding and manipulation of the hand tool by a user, said casing having a forward end and a rearward end,
  b. a piezoelectric vibratory element comprising an elongate bar of piezoelectric material and means mounting said bar in a forward portion of said tubular casing with the bar extending longitudinally of the casing, said mounting means comprising support means in said casing supporting said bar at a node of vibration so as to inhibit transmission of vibration to said casing, c. a vibratable work-tip disposed forwardly of the forward end of said casing and means coupling said work-tip with said vibratory element to transmit vibration from said element to the work-tip, d. signal generating means housed in a rearward portion of said casing, said signal generating means comprising an oscillator for generating an alternating electrical signal of ultrasonic frequency, said generating means being spaced from and mechanical vibrationally insulted from said piezoelectric vibratory element in said forward portion of said casing, e. circuit means wholly within said casing for electrically connecting said signal generating means with said piezoelectric vibratory element to apply said ultrasonic alternating electric signal to said piezoelectric vibratory element and thereby excite said element into ultrasonic vibration, f. said casing comprising a metallic sheath enclosing and electrically shielding said signal generating means, said piezoelectric vibratory element and said circuit means, g. means for connecting said signal generating means to a source of low voltage direct current for energizing said signal generating means, and h. manually operable means on said casing for controlling the supply of said low voltage direct current to said signal generating means and thereby controlling the operation of said signal generating means.

14. A hand tool according to claim 13, in which said circuit means comprises flexible leads providing electrical connections between said signal generating means and piezoelectric vibratory element while inhibiting transmission of mechanical vibration from said vibratory element to said signal generating means.

15. A hand tool according to claim 13, in which said elongate bar of piezoelectric material is of rectangular cross section and has control electrodes affixed to opposite sides of said bar at a node of vibration of said bar, and in which said circuit means comprises leads extending from said signal generating means and connected to said electrodes at a node of vibration of said bar to provide electrical connection of said signal generating means with said piezoelectric vibratory element while inhibiting transmission of mechanical vibration from said vibratory element to said signal generating means.

16. A hand tool according to claim 13, in which said circuit means comprises means for feeding a control signal from said piezoelectric element to said signal generating means to control the frequency of said oscillator.

17. A hand tool according to claim 13, comprising means for supplying a fluid cooling medium to said signal generating means and to said piezoelectric vibratory element and manually operable means on said casing for controlling the supply of said cooling medium.

18. A hand tool for creating and applying ultrasonic vibration especially for dental, medical and cosmetic use, comprising:

a. handle means comprising a tubular casing of slender elongage form to facilitate holding and manipulation of the hand tool by a user, said casing having a forward end and a rearward end, b. A piezoelectric vibratory element comprising an elongate bar of piezoelectric material and means mounting said bar in a forward portion of said tubular casing with the bar extending longitudinally of the casing, said mounting means comprising support means in said casing supporting said bar at a node of vibration so as to inhibit transmission of vibration from said bar to said casing, c. A vibratable work-tip disposed forwardly of the forward end of said casing and means coupling said work-tip with said piezoelectric vibratory element to transmit vibration from said element to said work-tip, d. signal generating means dipsosed in a rearward portion of said casing, said signal generating means comprising an oscillator for generating an alternating electrical signal of ultrasonic frequency, said generating means being spaced from and mechanical vibrationally insulated from said piezoelectric vibratory element in said forward portion of said casing, e. circuit means wholly within said casing for electrically connecting said signal generating means with said piezoelectric vibratory element and thereby excite said element into ultrasonic vibration and by such vibration to produce ultrasonic vibration of said work-tip, f. electrical conductor means electrically connected with said signal generating means and extending from the rearward end of said casing for supplying low voltage direct current to said signal generating means in said casing, and g. fluid supply means comprising flexible fluid conduit means extending from the rearward end of said casing to a fluid supply, and fluid passage means extending longitudinally through said casing from said fluid conduit means at the rearward end of the casing to said work-tip at the forward end of the casing, said fluid passage means comprising a rearward portion in heat receiving relation to said signal generating means to cool the same, a forward portion in heat receiving relation to said vibratory element to cool the same, and a flexible intermediate portion between said rearward portion and said forward portion to provide continuity of said fluid passage means while providing mechanical vibrational insulation of said signal generating means.

19. A hand tool according to claim 18, comprising manually operable means on said casing for controlling flow of fluid through said passage means.

20. A hand tool according to claim 18, in which said coupling means comprises a connector fixed on the forward end of said bar of piezoelectric material and having means for removably holding said work-tip and a fluid passage connected with said forward portion of said fluid passage means and extending to said work-tip.

21. A hand tool according to claim 20, in which said work-tip has a tubular portion connected with said fluid passage of said connector.

22. A hand tool according to claim 18, in which said signal generating means comprises a power transistor and a heat sink in thermally conducting relation to said power transistor, said rearward portion of said fluid passage means comprising a fluid passage through said heat sink.

* * * * *